United States Patent
McNair et al.

(10) Patent No.: US 9,542,532 B1
(45) Date of Patent: Jan. 10, 2017

(54) DECISION SUPPORT RECOMMENDATION OPTIMIZATION

(71) Applicant: Cerner Innovation, Inc., Lenexa, KS (US)

(72) Inventors: Douglas S. McNair, Leawood, KS (US); John Christopher Murrish, Overland Park, KS (US); J. Bryan Ince, Manly (AU)

(73) Assignee: CERNER CORPORATION, Lenexa, KS (US)

( * ) Notice: Subject to any disclaimer, the term of this patent is extended or adjusted under 35 U.S.C. 154(b) by 429 days.

(21) Appl. No.: 13/646,356

(22) Filed: Oct. 5, 2012

Related U.S. Application Data

(60) Provisional application No. 61/544,819, filed on Oct. 7, 2011.

(51) Int. Cl.
*G06F 19/00* (2011.01)
*G06Q 50/24* (2012.01)
*G06N 5/04* (2006.01)

(52) U.S. Cl.
CPC ............... *G06F 19/345* (2013.01); *G06N 5/04* (2013.01); *G06Q 50/24* (2013.01)

(58) Field of Classification Search
None
See application file for complete search history.

(56) References Cited

U.S. PATENT DOCUMENTS

| 5,615,341 | A | 3/1997 | Agrawal et al. |
| 6,651,049 | B1 * | 11/2003 | Agrawal et al. ............ 707/694 |
| 6,754,651 | B2 | 6/2004 | Nanavati et al. |
| 7,050,988 | B2 | 5/2006 | Atcheson et al. |

(Continued)

OTHER PUBLICATIONS

Sager, Naomi, et al. "Natural language processing and the representation of clinical data." Journal of the American Medical Informatics Association 1.2 (1994): 142-160.*

(Continued)

*Primary Examiner* — Kakali Chaki
*Assistant Examiner* — Daniel Pellett
(74) *Attorney, Agent, or Firm* — Shook Hardy & Bacon L.L.P.

(57) ABSTRACT

Systems, methods, and computer-readable media are provided for facilitating clinical decision making by directing the emission of computer-generated health-care related recommendations towards contexts in which the recipient will likely find the recommendations salient and will likely welcome them and act upon them. 'Uptake' of computer-generated recommendations for diagnostic tests or therapeutic interventions is thereby substantially increased, and 'alert fatigue' is substantially decreased. Embodiments of our technology overcome certain drawbacks associated with the prior art by providing a means for ascertaining which decision-support recommendations are likely to be favorably considered by the recipient and acted-upon (recommendation 'uptake'). System and method embodiments for providing a predicted probability of user uptake of a context-specific system-generated recommendation patient are disclosed herein and for applying that information to decide whether or not to emit the relevant recommendation.

20 Claims, 11 Drawing Sheets

(56) References Cited

U.S. PATENT DOCUMENTS

| | | | |
|---|---|---|---|
| 7,080,052 B2 | 7/2006 | Busche | |
| 7,113,917 B2 | 9/2006 | Jacobi et al. | |
| 7,370,033 B1* | 5/2008 | Roychowdhury | 707/602 |
| 7,386,485 B1 | 6/2008 | Mussman et al. | |
| 7,433,879 B1 | 10/2008 | Sharma et al. | |
| 7,672,865 B2 | 3/2010 | Kumar et al. | |
| 7,676,400 B1 | 3/2010 | Dillon et al. | |
| 7,698,170 B1 | 4/2010 | Darr et al. | |
| 7,720,720 B1 | 5/2010 | Sharma et al. | |
| 2006/0253296 A1* | 11/2006 | Liisberg et al. | 705/1 |
| 2007/0067181 A1* | 3/2007 | Dettinger et al. | 705/2 |
| 2008/0243547 A1* | 10/2008 | Brett et al. | 705/3 |

OTHER PUBLICATIONS

Moon, Hojin, et al. "Ensemble methods for classification of patients for personalized medicine with high-dimensional data." Artificial intelligence in medicine 41.3 (2007): 197-207.*

Davis Darcy A., et al. "Time to CARE: a collaborative engine for practical disease prediction." Data Mining and Knowledge Discovery 20.3 (2010): 388-415.*

* cited by examiner

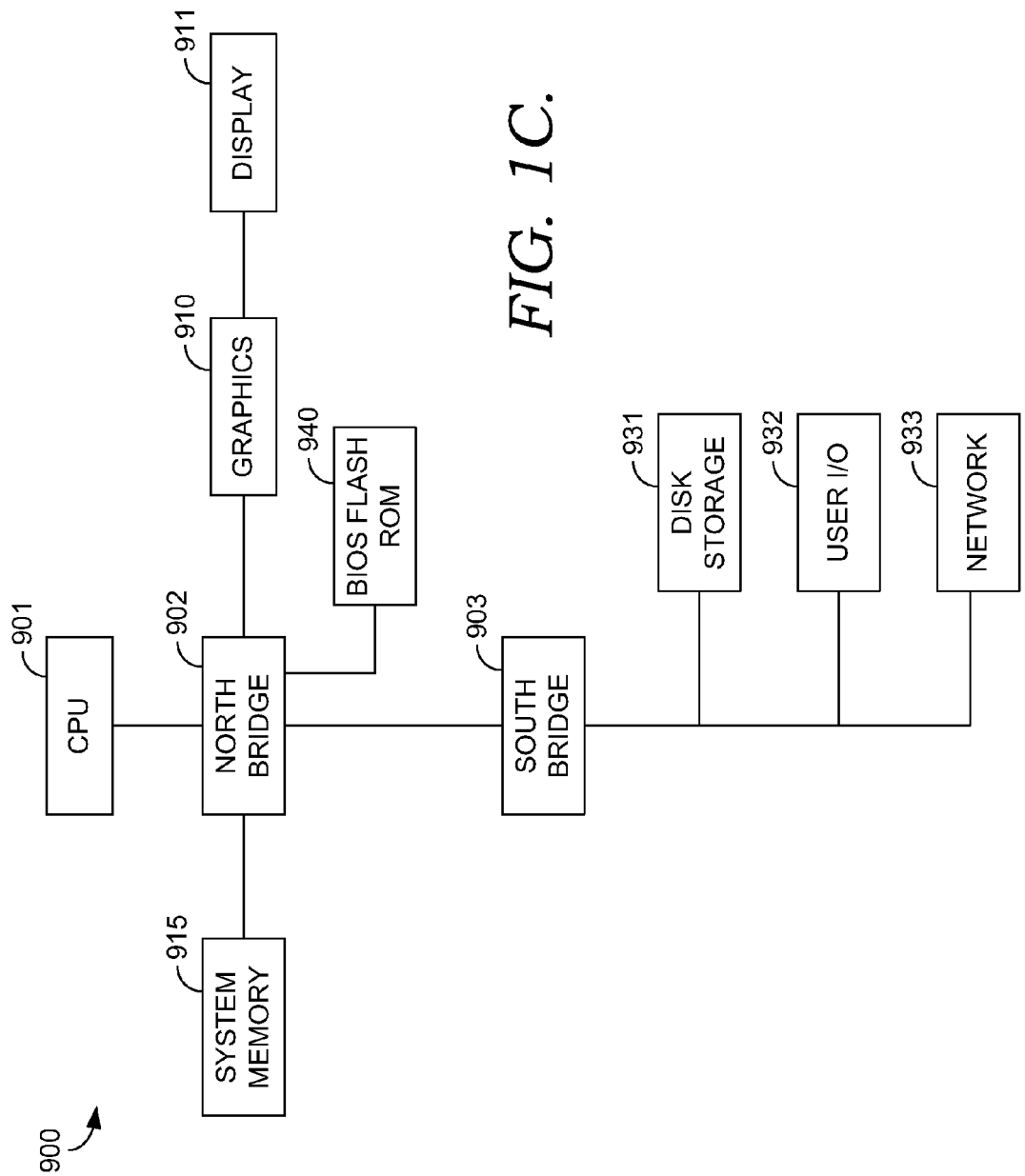

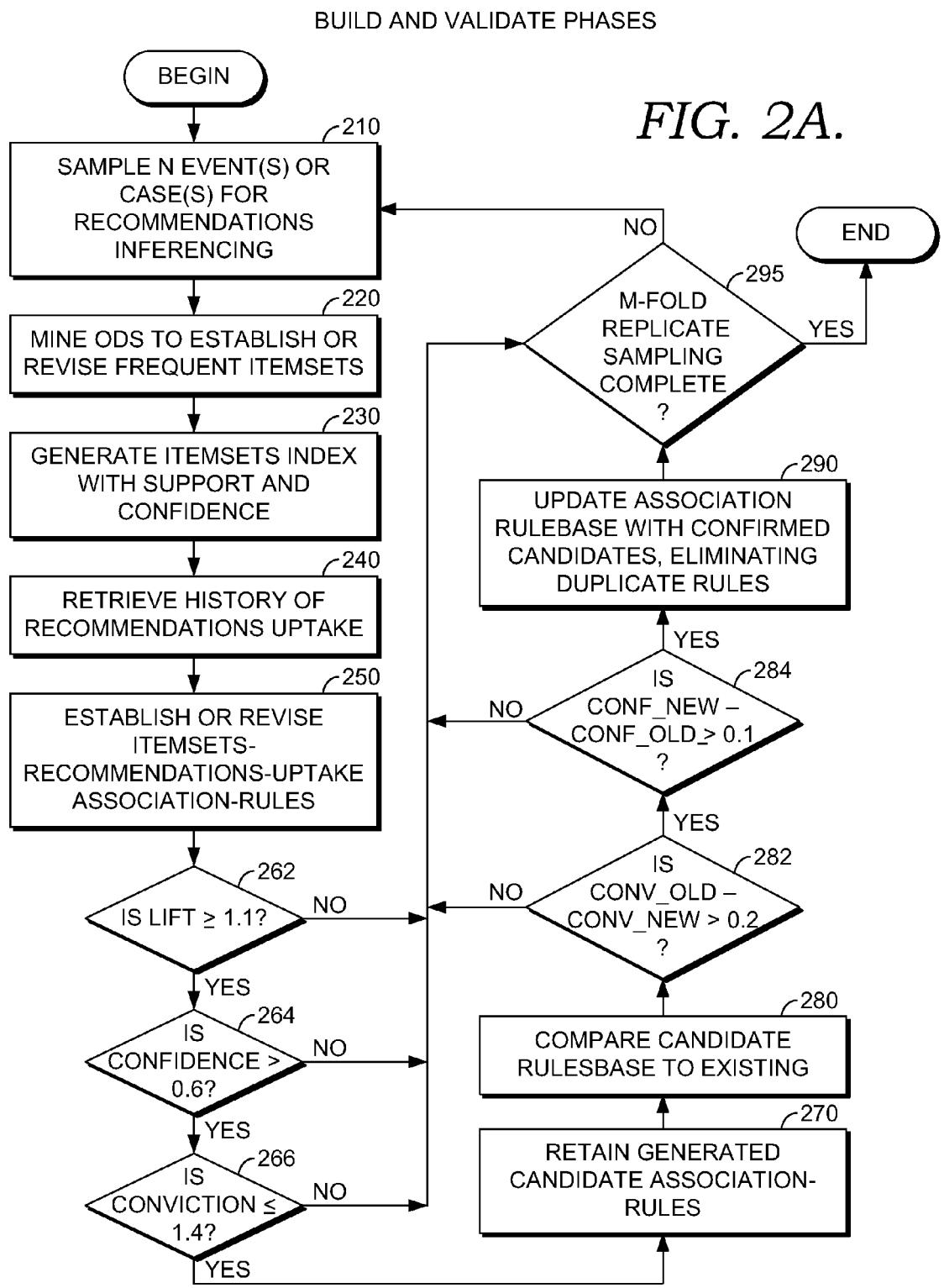

```
Rule 001: (21.9/6.2, lift 1.5)
        polyp_nbr > 1
        ->  class 1    [0.700]
Rule 002: (64.4/25, lift 1.2)
        prev_cspy_nbr <= 1
        ->  class 0    [0.609]
Rule 003: (146.9/67.7, lift 1.1)
        recency > 2
        ->  class 1    [0.538]
Rule 004: (22.1/4.3, lift 1.5)
        recency <= 2
        ->  class 0    [0.781]
Rule 005: (62.1/28.2, lift 1.2)
        prev_cspy_nbr > 2
        ->  class 1    [0.545]
Rule 006: (23.4/7.1, lift 1.3)
        age > 77
        polyp_nbr = 0
        ->  class 0    [0.680]
Rule 007: (9.1/1, lift 1.6)
        payor = M
        prev_cspy = 0
        ->  class 0    [0.817]
Rule 008: (19.1/6.9, lift 1.4)
        payor = M
        teach = 1
        ->  class 1    [0.625]
Rule 009: (27.5/9.4, lift 1.2)
        payor = B
        ->  class 0    [0.648]
Rule 010: (9/1, lift 1.6)
        payor = C
        recency > 2
        polyp_nbr = 0
        ->  class 0    [0.815]
Rule 011: (30.4/12.3, lift 1.2)
        payor = A
        ->  class 1    [0.590]
Rule 012: (14/2, lift 1.5)
        age > 80
        recency > 4
        ->  class 0    [0.813]
Rule 013: (12/1, lift 1.6)
        age > 63
        prev_cspy = 0
        ->  class 0    [0.857]
Rule 014: (150.7/60.5, lift 1.1)
        pcp = 1
        ->  class 0    [0.597]

Rule 015: (24.5/7.9, lift 1.5)
        recency > 2
        pcp = 0
        ->  class 1    [0.666]
Rule 016: (12.3/1.9, lift 1.9)
        payor = M
        recency > 7
        teach = 1
        prev_cspy = 1
        ->  class 1    [0.800]
Rule 017: (30.4/12.3, lift 1.2)
        payor = A
        ->  class 1    [0.590]
Rule 018: (14/2, lift 1.5)
        polyp_nbr > 1
        ->  class 1    [0.813]
Rule 019: (9/1, lift 1.6)
        crc_fh = 1
        ->  class 1    [0.815]
```

FIG. 4.

| Colonoscopy Example: Actual *vs.* Predicted Recommendation Uptake | | |
|---|---|---|
| Predicted Uptake\Actual Uptake | Accepted Recommendation | Declined/Overrode Recomm. |
| Acceptor | 63 | 38 |
| Decliner/Overrider | 31 | 68 |

Chi-square (Yates-corrected): 18.1, $p < 0.0001$; Sensitivity: 67%; Specificity: 64%; Odds ratio: 3.64.

DECISION SUPPORT RECOMMENDATION OPTIMIZATION

CROSS-REFERENCE TO RELATED APPLICATIONS

This application claims the benefit of U.S. Provisional Application No. 61/544,819, titled "Decision-Support Recommendation Optimization," filed Oct. 7, 2011, which is hereby expressly incorporated by reference in its entirety.

SUMMARY

Systems, methods, and computer-readable media are provided for facilitating clinical decision making by directing the emission of computer-generated health-care related recommendations towards contexts in which the recipient will likely find the recommendations salient and will likely welcome them and act upon them. In one embodiment, a method is provided for determining whether to emit a recommendation comprising generating frequent itemsets and association rules from a data set comprising an operational data store containing past events and transactions from this user as well as numerous other users, including data as to what recommendations were previously made and what action (uptake) they received; cross-validating and filtering the association rules such that each retained association rule has properties that denote relevance and predictive power with regard to predicting recommendation uptake; receiving an event and recommendation context from the user and from the information system; using the recommendation context at a computer system to identify a plurality of candidate recommendations predicted by the association rules to match the recommendation context; ranking the plurality of candidate recommendations using the score for each candidate association rule to identify at least a highest ranking candidate association rule; issuing the qualifying candidate recommendations. In some embodiments the method further comprises logging the user's subsequent action, if any, for use in successive repeated analyses and enhancement of the association rulebase with regard to its accuracy in predicting recommendations uptake.

BRIEF DESCRIPTION OF THE DRAWINGS

Embodiments of the invention are described in detail below with reference to the attached drawing figures, wherein:

FIGS. 1A, 1B and 1C depict aspects of an illustrative operating environment suitable for practicing embodiments of the invention;

FIGS. 2A, 2B and 2C depict a flow diagram depicting embodiments of a method for building and validating association-rules for a decision support recommendation service;

FIG. 4 illustrates an exemplary display showing results of recommendation optimization for a patient eligible for colorectal cancer screening and scheduling of colonoscopy;

FIG. 5 depicts a representative display of actual vs. predicted recommendation update for the example associated with FIG. 4.

DETAILED DESCRIPTION

Figure 1A:
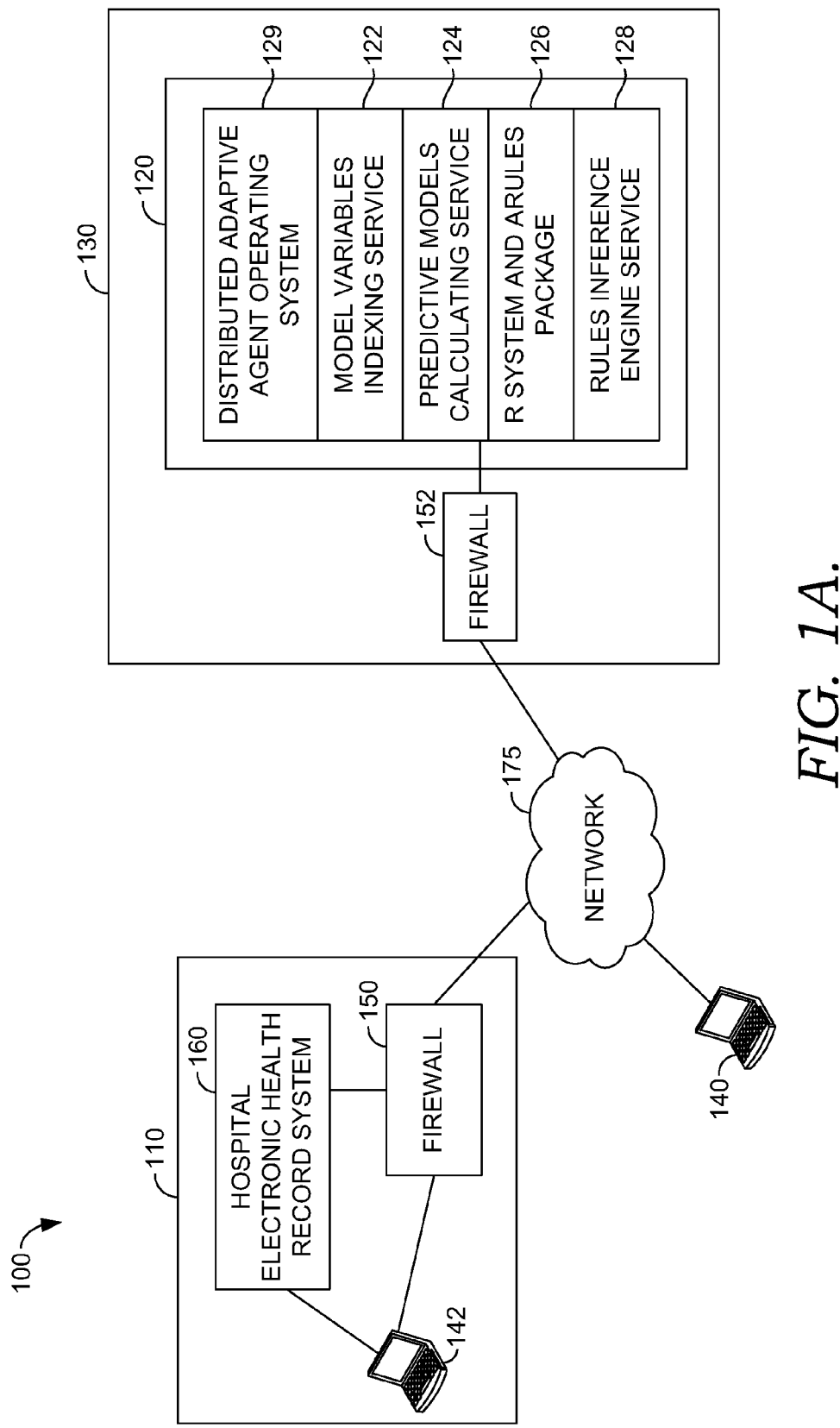

The subject matter of embodiments of our invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable and nonremovable media, and contemplates media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

Timely, salient recommendations provided by an automated decision-support system to clinicians or to consumers can significantly enhance the quality of care and the achievement of health outcomes and care process measures. However, computer-generated recommendations that arrive at inopportune times; that are presented to individuals whose role and authority and responsibilities as contributors to planning or executing the patient's care are discordant with the role and authority entailed by the recommendations; or are in other ways not sufficiently 'salient' to the recipient's goals and priorities may be, at best, useless or, at worst, harmful. The time that the recipient takes to dismiss or override the nonsalient recommendations may be wasted, and the recipient may be distracted by cognitive effort or annoyed by the compulsion to receive and dispose of those things that they regard as intrusive or extraneous advice.

Additionally, an expert system or decision-support systems, particularly one operating in a health care environment, should be an asset that increases the effectiveness and acts as a benefit to health care providers. A decision support system should be capable of providing advice conditioned upon the context (including, for example, the day-of-week and time-of-day; the antecedent patterns of the patient's illness or comorbid conditions including past medical history; the existing plan of care and schedule of the patients treatments and the logistics pertaining to them; the patient's family history and social history; the prior informed consent (or not) related to interventional procedures that may be the subject of practice guidelines or standard-of-care recommendations; the patient's age; other demographic variables that may relate to the patient's assent or not to receive recommended interventions; the details of the clinician's location and role and responsibilities on behalf of the patient; the history with regard to accepting or declining previous recommendations emitted by the system; the insurance plan or payor(s) that will be covering any care services that might be recommended by the system; and other attributes of the patient, consumer, payor, and health system.

Decision-support recommendations that must be unremittingly and continuously ignored or overridden lead to alert fatigue on the part of the user. 'Alert fatigue', which has become increasingly frequent in the medical literature, refers to the distraction and blunting of attention that can be caused by receiving an excessive number of well-intentioned but non-salient automated recommendations per unit time.

'Alert fatigue' does not assert that any of the recommendations or all recommendations are irrelevant per se. Indeed, many of the recommendations may be highly relevant in terms of conforming to generally-accepted practice guidelines or standards of care and objectives of care quality and safety. Nonetheless, if the recommendations are ignored or overridden in a large percentage of instances, then the benefit of the system's automatically emitting the recommendations is not achieved, and significant risks and wasted time and attention will occur. Thus, it is desirable that automated decision-support expert systems emit appropriate recommendations when the attributes and context indicate that the recommendations are likely to be welcomed and accepted. Conversely, it is also desirable that such systems refrain from emitting recommendations when the attributes and context indicate that the recommendations are likely to annoy the recipient and will not be accepted and acted-upon.

A technology is provided for facilitating clinical decision making by controlling the emission of computer-generated health-care related recommendations. Embodiments of the invention thus provide systems, methods, and computer-readable media for continually tracking the clinical and physiologic status of a patient in a hospital. At least some of the embodiments allow physicians, nurses and clinical researchers to provide more safe and effective care for each patient, especially those who have admissions lasting several days or more. In addition or alternatively, at least some embodiments assist the electronic health record system to determine whether or not to emit decision-support recommendations regarding the personalized care of the patient. More specifically, some embodiments ascertain association-rule patterns that predict users' uptake (or acceptance) of system-generated recommendations and the salience of various recommendations that are nominally valid to make and tailor the automatic emission or withholding of recommendations according to the pattern(s) that prevail at the time of the recommendation-worthy event.

At a high level, embodiments of our technology provide a means for ascertaining which decision-support recommendations are likely to be favorably considered by the recipient and acted-upon (recommendation 'uptake'). In some embodiments, there is provided a system and method for generating association rules denoting multi-variable patterns under which the user is likely to accept or, alternatively, likely to ignore or override the applicable recommendation. Accordingly, one embodiment of a system includes, for example, a data module receiving data relating to a patient's clinical and laboratory variables, the provider's profile and role and location, a data transformation and statistical computation module generating an output from the data, the output representing the likelihood of the user's uptake of system-generated recommendation, and a display module displaying the output.

In addition to the features of embodiments of the recommender system and its uses thereof, it is further contemplated that an exemplary use of some embodiments may include the use of a natural-language parser, enabling embodiments of the recommender system (and the association-rules that it compiles during the build-and-validate phases) to index and codify variables that are represented in textual expressions in the health record. For example, in colonoscopy the number of polyps and their dimensions in centimeters are denoted by textstrings, which the parser may be invoked to index as concepts in an ontology, and bind numerical values that an association-rule mining algorithm can then utilize in pattern-building.

Figure 1B:
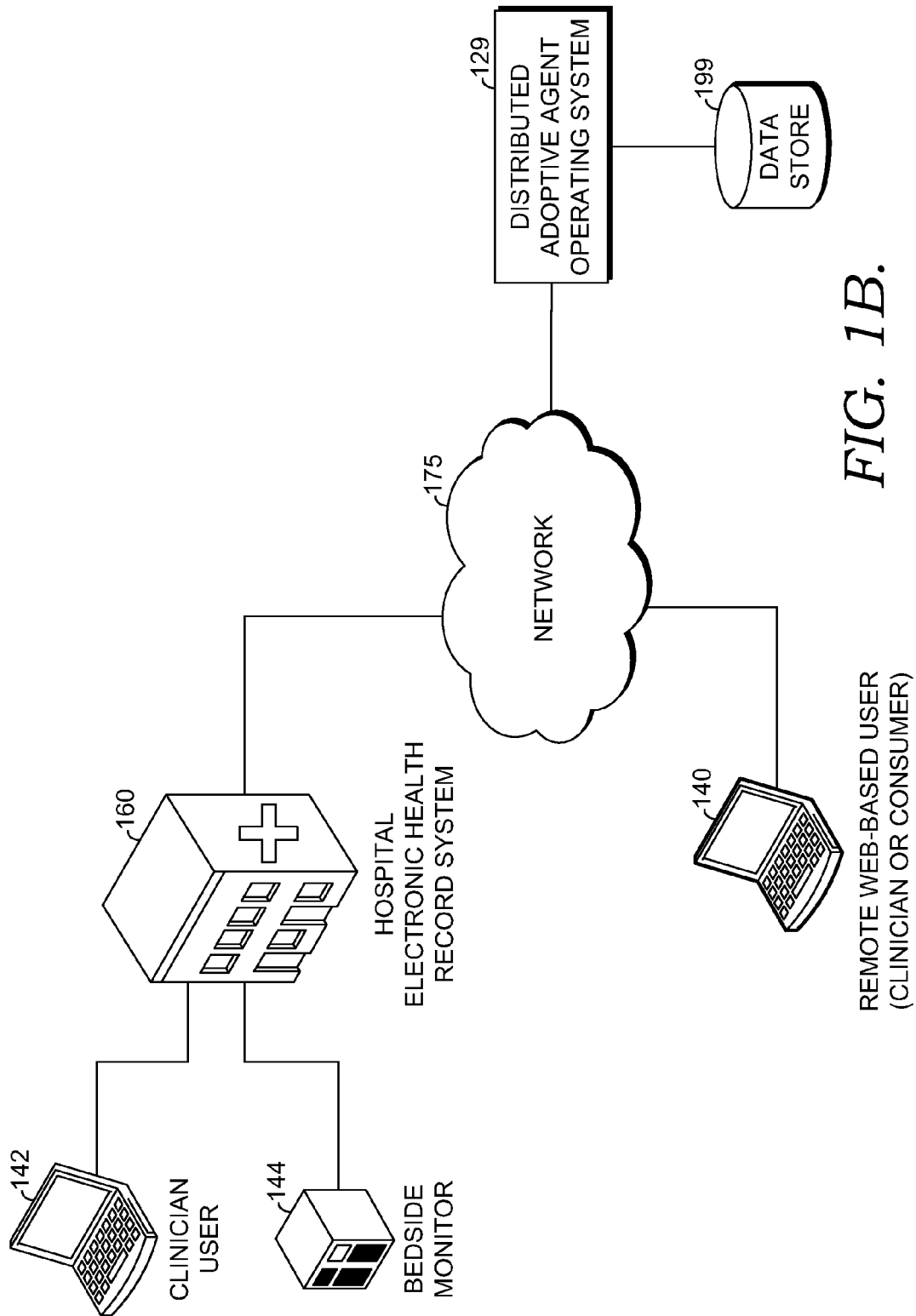

Turning now to FIGS. 1A and 1B, there is presented in 100 a system diagram of a computerized system for compiling and running an embodiment of a decision support recommendation service. With reference to FIG. 1A, a first premise location 110 includes a private network behind firewall 150. Client computers such as 142 communicate with Hospital electronic health record system 160 through a private network. In embodiments computers 150 and 160 are servers that run within a local or distributed private network. Computer systems such as server 120 within premise 130 connect through firewall 152 to a private network and to public network 175 such as the internet to other premise 110 equipment and also to public system user computer 140. Embodiments of computer software stack 121 run on a server such as 120 shown in FIG. 1A. Embodiments of software stack 121 run as a distributed system on a virtualization layer within computers such as 160 and 120. Embodiments of software stack 121 include a distributed adaptive Agent operating system 129 that hosts a number of services such as 122, 124, 126, and 128. Embodiments of software programs 122, 124, 126 and 128 run as a local or distributed stack on a collection of personal computers and servers such as 142, 120, 160, and 140. Variables indexing service 122 provide services that facilitate retrieving frequent item sets, extracting database records, and cleaning the records' variables' values. Software packages 126 perform statistical software operations, and in include statistical calculation packages such as, in one embodiment, the R system; R-system modules and arules packages. Calculating Service 124 and rules inference engine service 128 facilitates the computation of association rules and their evaluation and implementation. In one embodiment, association rules take the form of an association between two variables such as, for example, 80% of the time when a patient is over 90 years old, a recommendation to perform a colonoscopy will be ignored.

FIG. 1B illustratively depicts another example system diagram of a computerized system for compiling and running an embodiment of a decision support recommendation service. Some of the components of FIG. 1B are described above with respect to FIG. 1A. Also shown in FIG. 1B are bedside monitor 144, which can take the form of a patient bedside monitor, home monitor, or wearable monitor, for example, or similar device operable to provide information about one or more patients or users. In one embodiment, data store 199 includes patient data and information for multiple patients; variables associated with recommendations; recommendation context; recommendation ensemble; recommendation knowledge base; recommendation rules; recommendations; recommendation update statistics; operational data store, which stores events; frequent itemsets (such as "X often happens with Y", for example) and itemsets index information; association rulebases, agent libraries, and other information, patient-derived data, health care provider information, for example. Although depicted as a single data store, data store 199 may comprise more than one device located one or multiple locations, or in the cloud.

Turning now to FIG. 1C, there is shown one example of a computer system 900 that has software instructions for storage of data and programs in computer readable media. Computer system 900 is representative of a system architecture that could be used for computers such as 142, 120 and 160. One or more CPU's such as 901 have internal memory for storage and couple to the North Bridge device 902, allowing CPU 901 to store instructions and data elements in system memory 915, or memory associated with graphics card 910 which is coupled to display 911. Bios flash ROM 940 couples to North Bridge device 902. South bridge device 903 connects to north Bridge device 902 allowing CPU 901 to store instructions and data elements in disk storage 931 such as a fixed disk or USB disk, or to make use of network 933 for remote storage. User 10 device 932 such as a communication device, a mouse, a touch screen, a joystick, a touch stick, a trackball, or keyboard, couples to CPU through South Bridge 903 as well.

In some embodiments, computing system 900 is a computing system made up of one or more computing devices. In an embodiment, computing system 900 includes an adaptive multi-agent operating system, but it will be appreciated that computing system 900 may also take the form of an adaptive single agent system or a non-agent system. Computing system 900 may be a distributed computing system, a centralized computing system, a smart phone, a computer touch-pad, a single computer such as a desktop or laptop computer or a networked computing system.

In some embodiments, computing system 900 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. Provisional Patent Application No. 61/389,053, filed on Oct. 1, 2010, which is herein incorporated by reference in its entirety.

Figure 6:
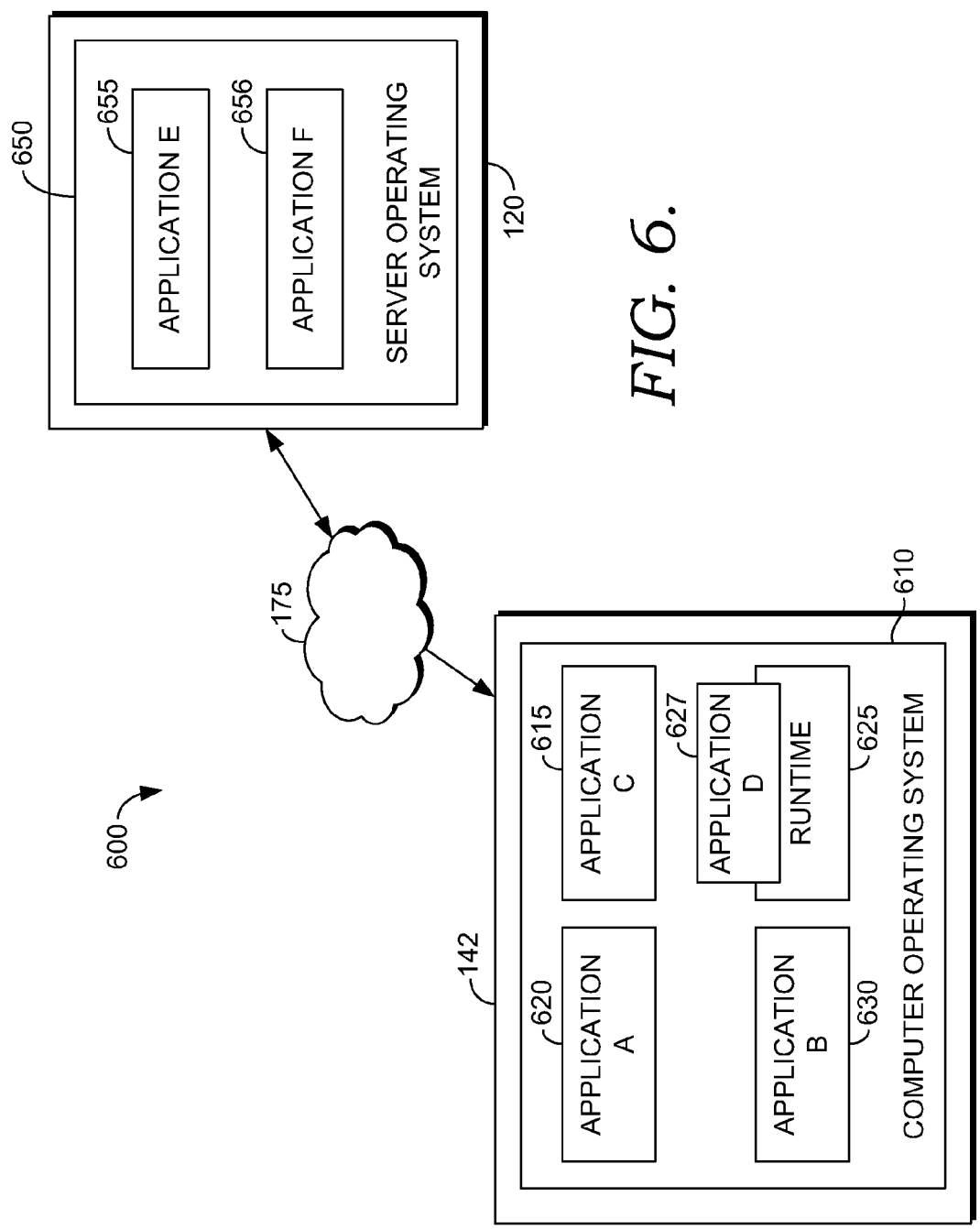
FIG. 6 depicts a context diagram of software components operable in embodiments to perform a computerized method.

FIG. 6 shows, in system 600 embodiments of software components such as Applications A (620), B (630), C (615), D (627), E (655), and F (656) that are operable individually or in any combination to carry out computer-usable instructions for performing a computerized method. Embodiments of a computerized method include a method of providing recommendations to a provider. Embodiments of a computerized method include a method of providing a decision support recommendation service. In embodiments a computer application A (620) runs on a computer operating system 610 on a computer 142. Embodiments communicate the results of steps performed by a first method in a component such as Application A (620) from computer 142 to an application E (655) on server 120 by communicating through network 175. In embodiments an application A (620) performs a first portion of the computerized method and generates data for a second part of the computerized method that is performed by application C (615). In embodiments an application D performs a first part of a computerized method by running within runtime environment 625, such as a Java™ runtime or a .Net™ runtime. In embodiments an application B 630 is a browser that presents a web page provided by remote server application E 655. Embodiments of software method components run a first portion of a method in server application E 655 and generate a message suitable for processing by a second server application F 656. In embodiments server applications E (655) and F (656) run on a server operating system 650.

Figure 2B:
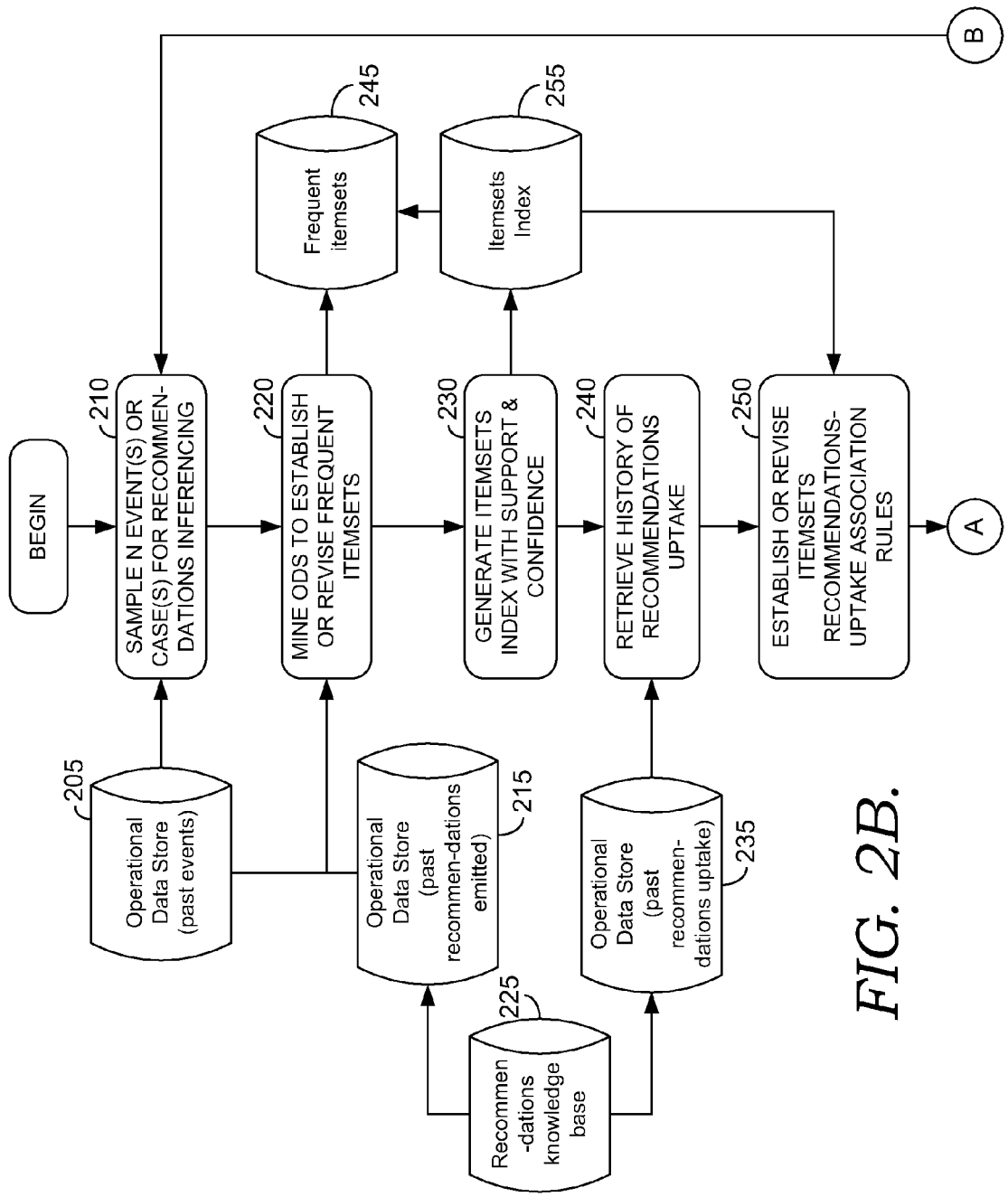
Figure 2C:
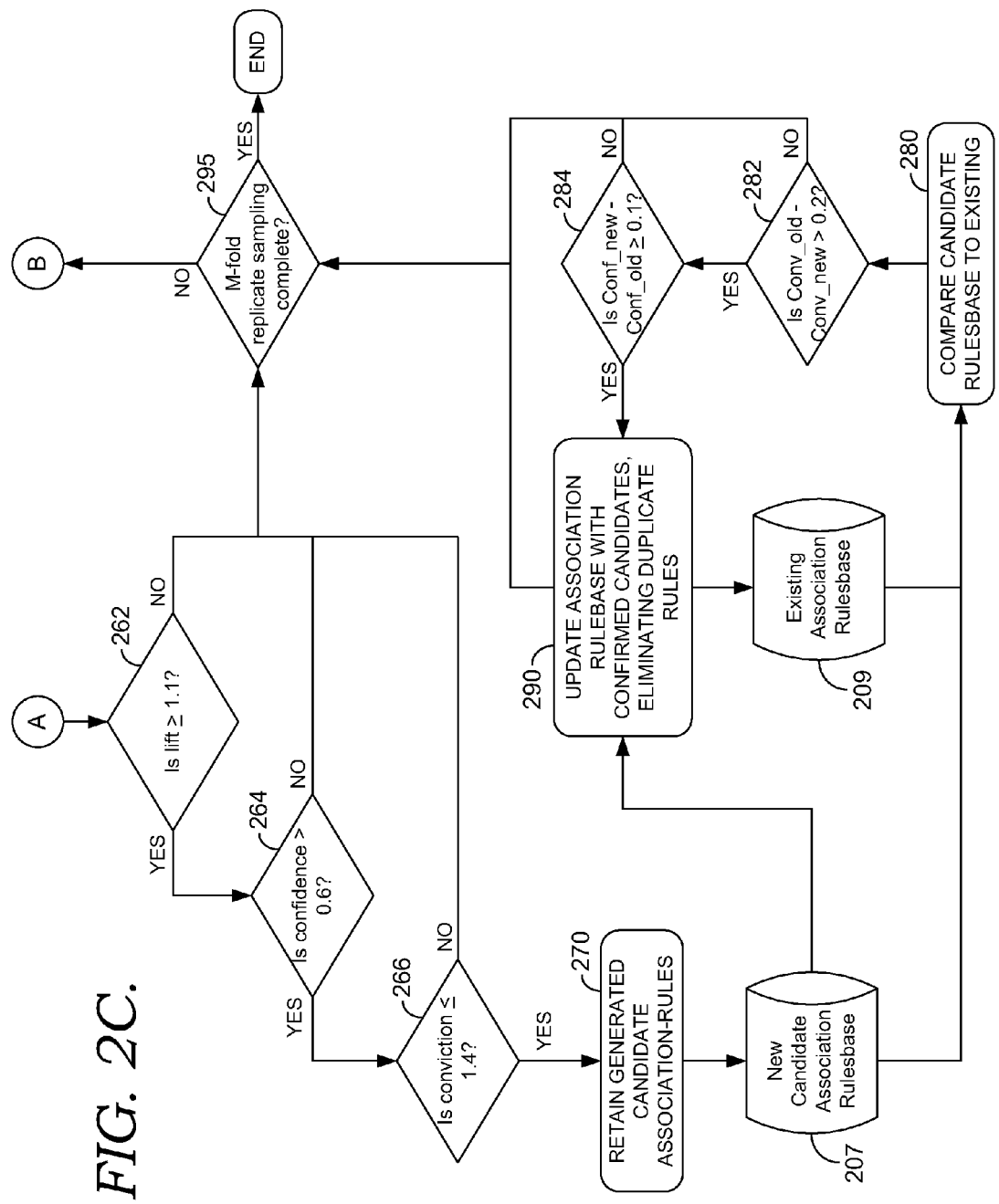

Turning now to FIGS. 2A, 2B and 2C, flow diagrams are provided depicting embodiments of a method for building and validating association-rules for a decision support recommendation service. Embodiments establish recommendation rules or revise recommendation rules. With reference to FIG. 2A, steps 210, 220, 230, 240 and 250 generate (or revise) association rules for itemset-recommendation acceptance. An operational data store contains information comprising a dataset documenting past events and transactions from one or more users. Embodiments of a dataset include data recording an action received (uptake) by a recommendation consumer.

In embodiments, an association-rule based recommendation is one that is based on historical transaction data. A feature set of n features is denoted $\{X_1, X_2, \ldots, X_n\}$. A recommendation consumer may take action Y. A set of transactions forms a context of care for a given patient. An ensemble is a set of contexts for a number of patients or for a number of providers that is typically used as a statistical basis for estimating parameters. Embodiments process an ensemble to determine a feature vector within a context that is indicative of a recommended action. In some embodiments, association rules may be defined as statements of the form $\{X_1, X_2, \ldots, X_n\} \rightarrow Y$, which implies that Y may prevail if $\{X_1, X_2, \ldots, X_n\}$ are all true antecedents. Here, "may" implies that a rule is only probable, not identical. Furthermore, in some embodiments where an item represents a recommended action, there can be a set of items indicated, not just a single item. A threshold (percentage) that a rule holds in all transactions is referred to as the rule's 'support'. A probability of finding Y in a context with all $\{X_1, X_2, \ldots, X_n\}$ is referred to as the rule's 'confidence'. A level of confidence that a rule must exceed is referred to as 'interestingness'. A ratio of the expected frequency that $\{X_1, X_2, \ldots, X_n\}$ occurs without Y (i.e., the frequency that the rule makes an incorrect prediction) if $\{X_1, X_2, \ldots, X_n\}$ and Y were independent divided by the observed frequency of incorrect predictions is referred to as the rule's 'conviction'. As is known to one skilled in the art, all of these metrics are examples of performance figures-of-merit for association rules.

Association rules are most commonly of the form "80% of the people who buy bread also buy butter". In other words, the association rules concern simultaneous actions or decisions taken by an individual, comprising a frequent itemset. More broadly, however, embodiments of association rules may be formulated to classify any consequent predicate Y with any set of antecedent features or predicates $\{X_1, X_2, \ldots, X_n\}$. For example, the computer user's favorable consideration of and action upon a system-generated recommendation may be a consequent predicate, which may or may not be synchronous with the antecedents. And the antecedent predicates may be variables whose values may be their present values or may be values, or mathematical functions of values, that prevailed in the past, either for the patient at hand or others whose attributes are similar, or for the provider at hand or others whose attributes are similar, or for the recommendation context at hand or others whose attributes are similar.

Association rules have potential applications in web-based ecommerce and many other fields beyond health care, but in any context there exist obstacles that must be addressed. Specifically, at a high level, the problem of discovering association rules can be generalized into two steps: (1) retrieving transaction data from the operational data store and finding frequent itemsets in the retrieved data, and (2) generating association rules from these frequent itemsets.

Embodiments of a method of providing a recommendation store medical transaction data in an operational data store 205. A provider computer system such as 142 retrieves the medical transaction data and assembles transaction data for a plurality of patients. Medical transaction data generally comprise data associated with a patient in a point of care facility. Embodiments assemble transaction data of discrete data elements such as transaction records that store codified items in a structural database. Embodiments retrieve data elements represented by coded concepts within a data dictionary or ontology. Embodiments assemble data that including data derived from a classification algorithm applied to unstructural documents that are collected using a search facility. Embodiments make use of a natural language processing algorithm for processing the unstructured textual documents. Embodiments accumulate a patient context, or a time series, of patient care transactions, selecting some qualifying events to form the context for a patient or for a provider, for a time window of past events prior to a point of care action. Qualifying events are those determined to be interesting for a chosen analysis.

Embodiments of medical transaction data include patient care type, patient type, patient age, patient history, institution type, venue, caregiver type, and primary payor identity. Examples of patient care operation type include registration processing, release processing, patient interview preparation, patient interview, patient interview recordation, lab process, patient instruction, patient advising, patient billing, patient fee collection, and medical procedure application. Examples of patient type include cardiac, general care, cancer, undiagnosed, etc. Examples of institution type include general hospital, clinic, outpatient, emergency, urgent care, teaching institution, and critical care. Example of venue include home care, outpatient, admitted, and clinical. Examples of caregiver type include clinician, nurse, nurse practitioner, administrative, general practitioner, and specialist. Examples of payor identity include self-pay, government, insurer, self-insurer and specific carrier insurer.

Some embodiments use Eclat, Apriori and other algorithms to perform step (1) above. Some embodiments perform Step (2) using commercial software systems or several open-source software packages including, for example, RuleQuest C5®; R system arules; Weka J48; StatSoft Statistics®, in some embodiments. In the example described below in connection to FIGS. 4 and 5, the Weka J48 algorithm was utilized, and aalidation testing was performed using Quinlan's C5 algorithm. In this example, computation of lift, confidence, and conviction were performed using native arithmetic functions in the Oracle relational database system. FIG. 4 shows a representative display 401 of association rules for colonoscopy recommendation uptake. FIG. 5 shows a representative display 502 useful for evaluating the performance of actual and predicted recommendations uptake.

Association rules systems applied to ecommerce applications may utilize an Apriori-like candidate itemsets generation and support-based approach. For typical clinical applications of interest, the number of dimensions present for the underlying variables and the number of members within a set for individual discrete variables (cardinality) rule generation can be a time-consuming process that entails huge memory requirements. Furthermore, when the threshold for minimum support is low (as is the case for most clinical applications, which address patients who, for example, may have any of numerous combinations of comorbid conditions), and hence the number of frequent itemsets is very large, most algorithms either run out of memory or exceed the allocated disk space due to the huge number of minimally-frequent itemsets. Therefore, some embodiment use a combination of lift, confidence, and conviction as performance criteria to prune the collection of generated itemsets and association rules. Furthermore, since memory and page-file requirements may still be very large, in some embodiments, a process of M-fold replication is performed, to determine that the generated and pruned association rulebase is stable (e.g., see step 295 of FIG. 2). Insofar as health care transaction information is increasingly in distributed repositories (e.g., Health Information Exchanges, or HIEs), embodiments of steps (1) and (2) may be implemented by a distributed, parallelized association rule mining algorithm such that multiple distributed adaptive agent processes execute on a plurality of computers that may be geographically disperse configuration according to the location of the health care transaction operational data stores, and communicate via the internet or via a private network with a 'master' agent that consolidates the resulting itemsets and association rules.

Continuing with FIG. 2A, at a step 210 events or cases are sampled for recommendation inferencing. Embodiments assemble transaction data into a context associated with each event. Embodiments form an ensemble of contexts for a recommendation, and use the ensemble as a basis of forming statistical measurements that derive rules from the assembled and collected information. An ensemble is a statistical sample such as a group of N cases including multiple instances where the recommendation was desirable, together with an associated context comprising time series data for a given patient and/or for a set of care providers. At a step 220 data from Operational Data Store (ODS) is mined for past event data store 215 and from transaction information data store 205 about a particular patient, or in some embodiments about multiple patients, and frequent itemsets are determined or revised and stored in frequent itemsets store 245. In some embodiments, the data mining is facilitated by a data-mining software agent. Embodiments operate on an ensemble of time series data for multiple contexts and perform a feature extraction algorithm on the ensemble to identify those variables and their associated values for an instance indicate a relationship between context and recommendation. At a step 230 an itemset index is generated and stored in itemsets index 255 with statistical support, confidence values, conviction values, and lift values. Embodiments compute lift as a ratio of the frequency of occurrence of an identified association targeting model divided by a random choice targeting model. Embodiments compute conviction as a rate of making a recommendation when the recommendation was not desired, or the frequency that the rule makes an incorrect prediction. Embodiments compute confidence as an estimated fraction of the population for which an association rule makes a recommendation when the recommendation is desirable. And at a step 240 a history of recommendation uptake or is retrieved from a data store, such as 225 or 235, if available, which includes information as to what recommendations were previously made and what action (uptake) they received. And at a step 250, itemsets-recommendations-uptake association rules are established or revised. In some embodiments at 250 lift, confidence and conviction are computed.

An exemplary embodiment processes an identified pattern for likelihood of predictive power. Embodiments compare the likelihood of predictive power to a threshold and retain those patterns as candidate patterns when the threshold level of performance is favorable. At steps 262, 264, and 266 statistical values for lift, confidence, and conviction are evaluated against threshold values as performance criteria so that only where the thresholds are exceeded is a rule likely to be salient to the recipient, in some embodiments. The specific threshold values depicted in steps 262, 264, 266, 282, and 284 are examples which may be associated with a set of patient data or conditions. These threshold values, in embodiments, take on a variety of values. Embodiments take the threshold values from a health care provider. Embodiments determine the threshold values by an agent. Some embodiments use a combination of lift, confidence, and conviction as performance tests to prune the collection of generated itemsets and association rules. Other embodiments use only one or two of these statistical tests. Embodiments use other statistical metrics in addition or substituting for these tests. Embodiments use operator feedback for evaluating performance criteria of the rules, which determine a given rule's performance.

An exemplary embodiment processes a rule for likelihood of predictive power by forming a comparison between a new candidate rule for a recommendation that is replacing an old rule for generating the same recommendation. Embodiments form a statistic comparing the new confidence to the old confidence as in decision box 284. Embodiments form a statistic comparing the new conviction rate to the old conviction rate as in decision box 282. Embodiments evaluate both conviction and confidence comparisons. Embodiments retain a new rule after a favorable comparison to an old rule. Embodiments retain an old rule after a favorable comparison to a new rule.

At steps 270, 280, 282, 284, 290 and 295, candidate association-rules are evaluated in order to determine whether to update an association rulebase with newly generated or revised rules. At 270 candidate association rules are retained, e.g. in a New candidate association rulebase 207. At 280 a comparison is made between a candidate rule and an existing rule. Embodiments of 270 assemble data from new and old rules in support of comparisons that restrict the replacement of existing rules. In some embodiments, the confidence values of the new rules are compared against confidence values of the old rules and only if the difference represents an improvement greater than a certain threshold (for example 0.1, as shown in step 284) is the new rule retained. In some embodiments, the conviction values of the new rules are compared against the conviction values of the old rules and only if the difference represents an improvement greater than a certain threshold (e.g. 0.2 as shown in 282) is the new rule retained. At 290 updated rules that pass the comparisons are stored in existing association rulebase 209. Embodiments eliminate duplicate rules. If a candidate association rule is rejected the method proceeds to 295 where a test is performed to determine if there is sufficient data available to produce a stable rule. If there is not enough data, the method returns to 210 to increase the amount of data samples used for rule construction, otherwise the method is complete.

FIG. 2B depicts another perspective of a building and validating association-rules for a decision support recommendation service. In some embodiments, build and validate association rules phase runs iteratively, continuously and in near-real time. In some embodiments, this phase runs nightly or periodically.

Figure 3A:
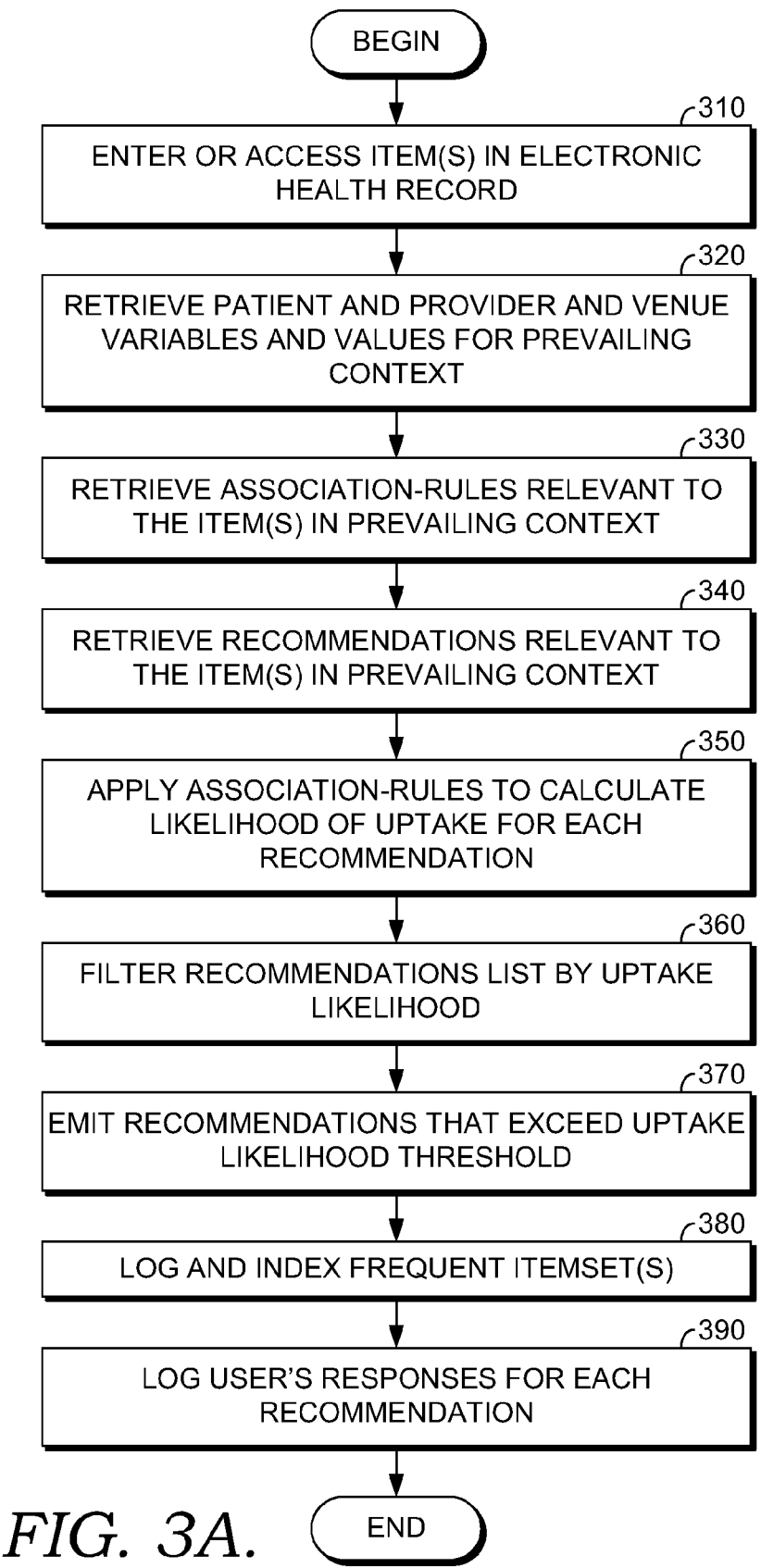
FIGS. 3A and 3B depict a flow diagram depicting embodiments of a method for evoking and applying association-rules for a decision support recommendation service.
Figure 3B:
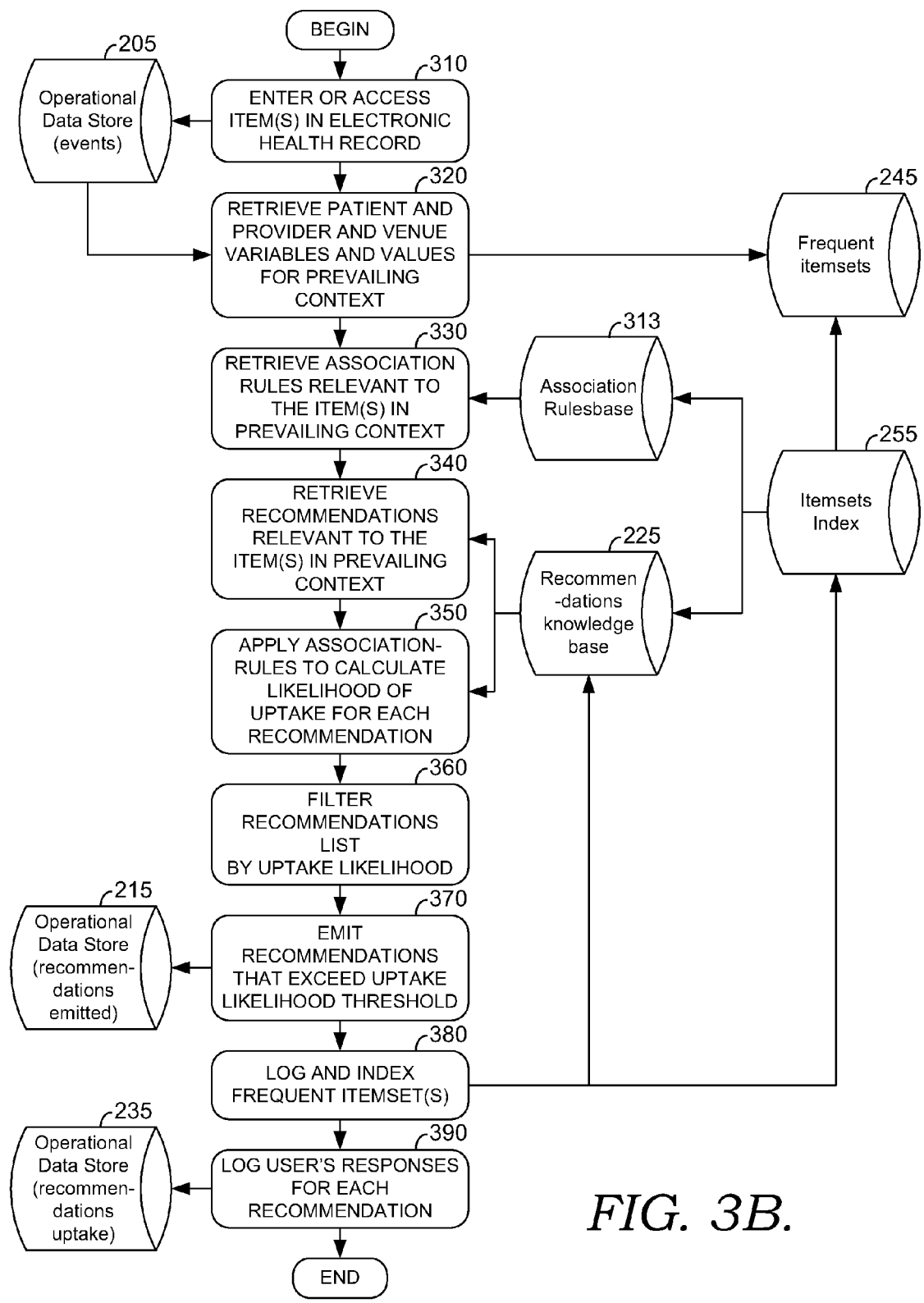

Turning to FIGS. 3A and 3B, flow diagrams are provided depicting embodiments of a method for evoking and applying association-rules for a decision support recommendation service. In embodiments this phase determines which association rules may be relevant, applies an association rules to calculate likelihood of uptake for each recommendation, and records information such as frequent itemsets and user-responses for each recommendation.

For example, in some embodiments, an event and recommendation context is initially received from the user and/or from the information system. The recommendation context is used to identify a plurality of candidate recommendations predicted by association rules to match the recommendation context. Embodiments rank the plurality of candidate recommendations using a score for each candidate association rule to identify at least a highest ranking candidate association rule. Embodiments determine a qualifying candidate association rule by comparing the scores of the candidate association rules to a threshold. Embodiments determine a qualifying candidate association rule by taking the highest scoring candidate association rule. Embodiments determine a qualifying candidate association rule by selecting the top scoring candidate association rule a certain fraction of the time, e.g. 50% of the time, in order to decrease the frequency of recommendations. Embodiments continually estimate lift, confidence and/or conviction, and evaluate one or more of these statistical estimates to determine whether or not a candidate recommendation meets a threshold level of quality based on one or more of these metrics. Qualifying candidate recommendations are issued, and a user's subsequent action, if any, is recorded for use in successive repeated analyses and enhancement of the association rulebase with regard to its accuracy in predicting recommendations uptake.

Accordingly, with reference to FIG. 3A, at a step 310 items in the electronic health record are accessed. At a step 320 patient and provider venue variables, and values for a prevailing context are retrieved. Embodiments of a computer application receive an event such as a point of care operation and a context for a provider and/or a patient and process context as a basis of determining association rules.

At a step 330 association rules relevant to the item(s) in the prevailing context are retrieved, e.g. from Association Rulebase 313. Embodiments process a context that consists of a set of variables and a set of values associated with the set of variables within a neighborhood of the present event. Embodiments match a number of recommendations to the context values and determine that the recommendations are relevant to the present context. Embodiments apply a set of screening rules to diminish the set of relevant recommendations based on the existence of subsets of the values of the variables that indicate a likely desire to not be presented with one or more recommendation. At a step 340, recommendations relevant to the item(s) in the prevailing context are retrieved. At a step 350, association-rules are applied to calculate the likelihood of uptake for the recommendation(s). At a step 360, the recommendations are filtered by likelihood of uptake. At a step 370, recommendations that exceed an uptake likelihood are emitted. Embodiments first generate the recommendation by a first Application A 620 forming a message that includes the relevant recommendation information to be sent to another software application such as Application C 615. Embodiments of generating a recommendation analyze a patient context looking for features that have been determined by a qualifying candidate recommendation, and generate a message when sufficient conditions are met. Embodiments of emitting a recommendation send an information message to a software application such as an operating system 610 on a system such as 142. Embodiments issue a recommendation by emitting a recommendation as a dialogue box displaying controls on display 911 including graphical controls such as buttons, check boxes, clickable graphical elements, touchable graphic elements, or elements that can be selected by a user through a keyboard. Such user selections are selected by the user manipulating a user I/O device 932. In embodiments, the likelihood threshold may be provided, determined by a software agent, or determined during the build and validate phases, further described in connection with FIGS. 2A and 2B.

At a step 380, frequent itemsets are logged and/or indexed. And at a step 390, the user's response, if any, is recorded. Embodiments collect information implied by the controls that are selected by a user in response to the user being presented with a dialogue box. Embodiments record elapsed time measuring substantially from a time that the dialogue box is presented to the user to an approximate time that a control is selected, or dismissed by a user. Embodiments record elapsed time measuring substantially from a time that the dialogue box is presented to the user to record that the recommendation was not acted upon within a certain time period. Embodiments track whether or not software related to a recommendation is invoked within a reasonable interval after the recommendation was presented to the user. Embodiments present a graphical user interface to a user with two controls, one to be selected if the user agrees with the recommendation, and a second to be selected by the user if the user does not consider the recommendation salient. Those actions that individually or collectively are indicative of the user accepting the recommendation, and taking it up into the practice of care is called generally "recommendation uptake". Embodiments accumulate the operational data associating uptake with the rule and storing the uptake status of the recommendation event within a computer, e.g., in data store 235.

FIG. 3B depicts another perspective of a method for evoking and applying association-rules for a decision support recommendation service.

With reference to FIG. 4 and FIG. 5, an illustrative example in clinical medicine is provided showing association rules for colonoscopy recommendation uptake. The example might be expressed as "80% of primary care doctors caring for a person who is between 50 and 77 years old, who has had more than 7 years elapse since their past colonoscopy, who receives his or her care at a teaching institution, whose location is clinic, whose patient type is outpatient, whose primary payor is X, and who has had colonoscopy at least once in the past, will accept a system-emitted recommendation to schedule a guideline-based recommendation of colonoscopy." The consequent predicate for this association rule is the doctor's acceptance or not of the recommendation to order colonoscopy at the time when features or events materialized such that colonoscopy is clinically indicated for the patient. The antecedent features for this association rule and recommendation context are the recommendation recipient's credential (e.g., MD or DO), specialty (one of class denoted as primary-care), the institution affiliation (teaching/academic), the payor (having its own policies with regard to colonoscopy frequency and other conditions for sanctioning such procedures), the recommendation setting in a clinic or other ambulatory care venue (as contrasted with an emergency department or in-patient location), plus a variety of other detailed attributes of the patient to whose care the colonoscopy recommendation pertains.

FIG. 4 depicts example textual output of a decision tree induction (DTI) algorithm. In some embodiments, the decision tree induction algorithm may be in a structured form capable of being ingested by a rules system maintainer, such as DiscernExpert for example. Some embodiments may take on a human-readable form such as the example shown in FIG. 4, which has 19 rules ranging from Rule 001 to Rule 019. In this example, each rule has one or more variables, such as "polyp_nbr>1 of Rule 001, indicating that the number of polyps of the patient exceeds 1. In this example, each rule is determined to be one of 2 classes, "class 1" or "class 0" indicating whether a recommendation should for a colonoscopy should be provided (class=1) or withheld (class=0, i.e. a recommendation to provide a colonoscopy will be ignored by the treating physician), and a corresponding confidence value between 0 ad 1 (shown in brackets next to each class) that indicates the confidence or certainty with which the corresponding predicate classification or prediction is made, based on a training dataset. For example, for Rule 001, for the Boolean condition polyp_nbr>1, the prediction of class 1 has a confidence value of 0.700. For more complex scenarios, more than 2 classes may exist. By way of another example, Rule 0016, has 4 variables and an 80% probability that the recommendation will be accepted, when the 4 variables are satisfied. Thus, when the payor equals "M" (i.e., Medicaid, Medicare or the public), the recency of the last colonoscopy is greater than 7 years, the health care facility is a teaching institution, and the previous colonoscopy is one, then there is an 80% likelihood that a recommendation to have a colonoscopy will be accepted by the treating physician or care provider.

In some embodiments, each rule of the DTI consists of: (a) a rule number, such as "Rule 001" which serves to identify the rule, and which may be arbitrary and generated automatically by the algorithm; (b) statistics that provide a summary of the performance of the rule, such as "(N, lift x)" or "(N/M, lift x)", where N represents a number of training cases covered by the rule and M (if it appears) represents how many of them do not belong to the class predicted by the rule; (c) one or more Boolean conditions that must all be satisfied if the rule is to be applicable, for example, polyp_nbr>1, as described above; (d) a class predicate asserted by the rule; and (e) the confidence value between 0 and 1 that indicates the confidence or certainty with which this predicate classification or prediction is made, based on the training dataset, as described above. The accuracy of the rule may be estimated by the Laplace ration (N−M+1)/(N+2). An information-theoretic 'lift' metric x is the result of dividing the rule's estimated accuracy by the relative frequency of the predicted class in the training set. The lift associated with each rule is given as:

$$\text{lift}(X \to Y) = \frac{\text{conf}(X \to Y)}{p(Y)}$$

Continuing with the illustrative example in clinical medicine of FIGS. 4 and 5, the rules shown in FIG. 4, generated by a Weka-based process described in connection to FIG. 2, and based on variable values for this patient, are used to predict whether the treating physician will find a recommendation salient and accept it or find it irrelevant and reject it.

FIG. 5 depicts a table of actual vs. predicted recommendation update for this example, and provides a characterization of how accurate the predictions were for the acceptors or decliners. As will be understood by those skilled in the art, sensitivity indicates a measure of true positives, and specificity indicates how frequent the false negatives occurred. Thus in this example, 67% of the time ((sensitivity of 67%), the treating physician accepted the recommendation.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

It will be understood that certain features and subcombinations are of utility and may be employed without reference to other features and subcombinations and are contemplated within the scope of the claims. Not all steps listed in the various figures need be carried out in the specific order described.

Additional example embodiments include:

A method, system for implementing the method, and computer-readable media having computer-usable instructions for performing the method of assembling transaction data for a plurality of patients and providers for identifying patterns usable to predict recommendation uptake, the method comprising: a) collecting serial medical data about the patient from a plurality of different inputs; b) collecting information about providers, including what each provider decided regarding each recommendation that was generated by the system; c) using the assembled data to identify patterns that are predictive of recommendation uptake and make decisions about the appropriateness of emitting or not emitting such recommendations when similar patterns subsequently materialize.

A method, system for implementing the method, and computer-readable media having computer-usable instructions for generating recommendations for possible action by a health care provider or consumer, comprising: generating frequent itemsets and association rules from a data set comprising an operational data store containing past events and transactions from this user as well as numerous other users, including data as to what recommendations were previously made and what action (uptake) they received; cross-validating and filtering the association rules such that each retained association rule has properties that denote relevance and predictive power with regard to predicting recommendation uptake; receiving a event and recommendation context from the user and from the information system; using the recommendation context at a computer system to identify a plurality of candidate recommendations predicted by the association rules to match the recommendation context; ranking the plurality of candidate recommendations using the score for each candidate association rule to identify at least a highest ranking candidate association rule; issuing the qualifying candidate recommendations; and logging the user's subsequent action, if any, for use in successive repeated analyses and enhancement of the association rulebase with regard to its accuracy in predicting recommendations uptake.

In some embodiments, further comprising generating one or more clinical or financial or operational recommendations selecting from a plurality of recommendations using attributes from the user's profile and role and venue, the patient's history and current clinical information, and, optionally, one or more predicates that are calculated from the patient's history and current information using a predictive statistical model.

In some embodiments, further comprising generating a recommendation message to include in a recommendation by using a profile itemset calculated from the recommendation context to select one or more relevant recommendation message from a repository of recommendation messages indexed by frequent itemsets and association rules.

In some embodiments, further comprising generating a recommendation message by using at least one attribute from each candidate association rule to select a recommendation message for that candidate association rule from a repository of recommendation messages.

In some embodiments, the step of determining the fitness for each candidate association rule comprises adjusting the predetermined scoring criteria if an estimate calculated from the recommendation context matches a target profile represented by a frequent itemset.

In some embodiments, the step of determining the fitness comprises calculating the lift, confidence, and conviction for each candidate association rule and testing whether the value of each is sufficient to predict the acceptance or nonacceptance of the recommendation(s).

In some embodiments, the step of determining the superiority of each candidate association rule in successive analyses comprises comparing the confidence of the new candidate association rulebase with the confidence of the existing production association rulebase.

In some embodiments, the step of determining the superiority of each candidate association rule in successive analyses comprises comparing the conviction of the new candidate association rulebase with the conviction of the existing production association rulebase.

In some embodiments, the step of determining the reliability of the candidate association rulebase in successive analyses comprises performing repeated replicated sampling using retrospective data and comparing the performance of the new candidate association rulebase and to the performance of the existing production association rulebase with the same data samples.

In some embodiments, the step of collecting medical data comprises retrieval of structured discrete data elements that are represented by coded concepts within a data dictionary or an ontology.

In some embodiments, the step of collecting medical data comprises retrieval and codification of items from unstructured textual documents by means of a search facility and natural language processing algorithm.

A method, system for implementing the method, and computer-readable media having computer-usable instructions for determining whether to emit a recommendation, comprising: collecting serial medical data about a patient from one or more inputs; collecting information about one or more health care providers or consumers including information indicating what each provider or consumer decided regarding a previous recommendation that was provided and information about one or more variables associated with that patient at the time of the recommendation; based on the collected information, determining a pattern indicating a likelihood of recommendation update associated with a condition of a patient; and based on the pattern, determining whether to emit a recommendation.

In some embodiments, the step of collecting medical data comprises retrieval of structured discrete data elements that are represented by coded concepts within a data dictionary or an ontology.

In some embodiments, the step of collecting medical data comprises retrieval and codification of items from unstructured textual documents by means of a search facility and natural language processing algorithm.

In some embodiments, steps of the methods described above and below are facilitated using a decision tree induction algorithm.

In some embodiments, further comprising determining whether to present a recommendation or silence it.

In some embodiments, further comprising logging a user's acceptance or rejection of a recommendation, and in some embodiments, logging information associated with the patient such as the patient's conditions, history, treatment facility, user's relationship with the patient (e.g., primary care giver or consulting physician) or other available information potentially relevant to a user's acceptance or rejection of a recommendation. In some embodiments, this information includes information specific to the user, such as, for example, the amount of time the user has been working, the number of patients the user is responsible for, the number of rejections or acceptances of recommendations the user has made with a window of time, such as within the past hour, day, week, or the total percentage of time the user accepts or rejects recommendations. A method, system for implementing the method, and computer-readable media having computer-usable instructions for determining whether to emit a recommendation, comprising: based on a set of operational data, including past events and transactions associated with a user indicating what recommendations were previously presented to the user and what action (uptake) was received by the user, determining frequent itemsets of associated recommendations and actions; based on frequent itemsets and the set of operational data, generating a set of association rules for generating recommendations; processing the set of association rules for relevance and likelihood predictive power; cross-validating and filtering the association rules such that each retained association rule has properties that denote relevance and predictive power with regard to predicting recommendation uptake; receiving a event and recommendation context from the user and from the information system; using the recommendation context at a computer system to identify a plurality of candidate recommendations predicted by the association rules to match the recommendation context; ranking the plurality of candidate recommendations using the score for each candidate association rule to identify at least a highest ranking candidate association rule; issuing the qualifying candidate recommendations; and, in some embodiments, receiving information associated with the user's subsequent action, if any information is present, so that such information may be used in successive repeated analyses and enhancement of the association rulebase with regard to its accuracy in predicting recommendations uptake.

The invention claimed is:

1. One or more non-transitory computer-readable storage devices having computer-executable instructions embodied thereon that when executed provide a method for providing recommendations to a provider based on transaction data for a plurality of patients, the method comprising:
   a) assembling transaction data for a plurality of patients;
   b) determining a patient context comprising serial medical data;
   c) generating a recommendation to a provider regarding the patient context;
   d) collecting information about provider acceptance of said recommendation;
   e) accumulating an ensemble of recommendation information;
   f) identifying a pattern that is predictive of recommendation acceptance over said ensemble; and
   g) determining to refrain from emitting a recommendation based on said pattern, the determining to refrain from emitting a recommendation comprising filtering the ensemble based on the pattern that is predictive of recommendation acceptance.

2. The one or more non-transitory computer-readable storage devices of claim 1, wherein the assembling of transaction data comprises retrieval of structured discrete data elements that are represented by coded concepts within a data dictionary or an ontology.

3. The one or more non-transitory computer-readable storage devices of claim 1, wherein the step of assembling transaction data comprises retrieval of codification items from unstructured textual documents using a search facility and natural language processing algorithm.

4. The one or more non-transitory computer-readable storage devices of claim 1, further comprising processing said pattern based on likelihood of predictive power.

5. The one or more non-transitory computer-readable storage devices of claim 4, wherein said step of processing comprises using statistical lift to determine whether or not to retain a candidate association rule within an association rulebase store.

6. The one or more non-transitory computer-readable storage devices of claim 4, wherein said step of processing comprises using statistical conviction to determine whether or not to retain a candidate association rule within an association rulebase store.

7. The one or more non-transitory computer-readable storage devices of claim 4, wherein said step of processing comprises using statistical confidence to determine whether or not to retain a candidate association rule within an association rulebase store.

8. The one or more non-transitory computer-readable storage devices of claim 6, further comprising evaluating a metric based at least in part on old statistical confidence and a new statistical confidence.

9. The one or more non-transitory computer-readable storage devices of claim 7, further comprising evaluating a metric based at least in part on an old statistical conviction and a new statistical conviction.

10. The one or more non-transitory computer-readable storage devices of claim 4, wherein said pattern comprises a multiple variable feature pattern.

11. A non-transitory computer-readable media having computer-executable instructions embodied thereon that when executed provide a method for providing a decision support recommendation service, the method comprising:

a) accumulating medical transaction data associated with a user including patient data for past events;

b) accumulating operational data indicating recommendations previously presented to a user and an action of the user associated with the recommendation;

c) determining a frequent itemset associating a recommendation and a user acceptance of said recommendation based on said action of a user;

d) generating a set of association rules for generating recommendations based on said operational data, said medical transaction data and said frequent itemset;

e) processing the set of association rules for likelihood of predictive power;

f) receiving an event and a recommendation context;

g) identifying a plurality of candidate recommendations predicted by the association rules to match the recommendation context;

h) determining to refrain from issuing a qualifying candidate recommendation based on the likelihood of predictive power with regard to predicting recommendation uptake.

12. The non-transitory computer-readable media of claim 11, wherein said medical transaction data comprises at least one of: patient care operation type, patient type, patient age, patient history, institution type, venue, caregiver type, and primary payor identity.

13. The non-transitory computer-readable media of claim 11, wherein said action of the user comprises at least one of: the user selecting a control in a graphical user interface, the user waiting at least a first predetermined period of time after a recommendation is presented before dismissing the recommendation, the user waiting at least a second predetermined period of time after a recommendation is presented before selecting a control in a graphical user interface, the user providing input indicative that a recommendation was considered, and the user providing input indicative that a recommendation was not considered.

14. The non-transitory computer-readable media of claim 11, further comprising processing said set of association rules for relevance.

15. The non-transitory computer-readable media of claim 14, wherein processing said set of association rules for relevance comprises applying a set of screening rules.

16. The non-transitory computer-readable media of claim 11, further comprising ranking the plurality of candidate recommendations using a score of each candidate association rule to identify at least a highest ranking candidate association rule.

17. The non-transitory computer-readable media of claim 11, further comprising generating a recommendation message by using at least one attribute from each candidate association rule to select a recommendation message for that candidate association rule from a repository of recommendation messages.

18. The non-transitory computer-readable media of claim 11, wherein said step of processing the set of association rules comprises using statistical lift to determine whether or not to retain a candidate association rule within an association rulebase store.

19. The non-transitory computer-readable media of claim 11, wherein said step of processing the set of association rules comprises using statistical confidence to determine whether or not to retain a candidate association rule within an association rulebase store.

20. A method for providing recommendations to a provider based on transaction data for a plurality of patients, the method comprising:

a) assembling transaction data for a plurality of patients;

b) determining a patient context comprising serial medical data;

c) generating a recommendation to a provider regarding the patient context;

d) collecting information about provider acceptance of said recommendation;

e) accumulating an ensemble of recommendation information;

f) identifying a pattern that is predictive of recommendation acceptance over said ensemble; and g) determining to refrain from emitting a recommendation based on said pattern, the determining to refrain from emitting a recommendation comprising filtering the ensemble based on said pattern.

* * * * *